(12) United States Patent
Sanger

(10) Patent No.: US 9,328,041 B2
(45) Date of Patent: May 3, 2016

(54) METHODS AND SYSTEMS FOR SEPARATING PARA-XYLENE USING A RADIAL FLOW SIMULATED MOVING BED CHAMBER

(71) Applicant: UOP LLC, Des Plaines, IL (US)

(72) Inventor: Robert J. Sanger, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 276 days.

(21) Appl. No.: 14/035,096

(22) Filed: Sep. 24, 2013

(65) Prior Publication Data

US 2015/0087876 A1 Mar. 26, 2015

(51) Int. Cl.
*C07C 7/12* (2006.01)
*B01D 15/18* (2006.01)

(52) U.S. Cl.
CPC ............... *C07C 7/12* (2013.01); *B01D 15/185* (2013.01)

(58) Field of Classification Search
None
See application file for complete search history.

(56) References Cited

U.S. PATENT DOCUMENTS

| | | | |
|---|---|---|---|
| 3,686,342 A | 8/1972 | Neuzil | |
| 3,917,734 A | 11/1975 | deRosset | |
| 4,108,915 A | 8/1978 | Rosback et al. | |
| 5,268,523 A | 12/1993 | Fellmann et al. | |
| 5,433,847 A | 7/1995 | Rice | |
| 5,565,104 A | 10/1996 | Priegnitz | |
| 5,884,777 A | 3/1999 | Pan et al. | |
| 6,325,940 B1 | 12/2001 | Ikeda | |
| 7,473,368 B2 | 1/2009 | Hotier | |
| 7,635,795 B2 | 12/2009 | Lee et al. | |
| 7,649,124 B2 | 1/2010 | Lee et al. | |
| 7,915,471 B2 | 3/2011 | Leflaive et al. | |
| 8,013,202 B2 | 9/2011 | Lee et al. | |
| 8,241,492 B1 | 8/2012 | Yuan | |
| 8,404,918 B2 | 3/2013 | Frey | |
| 2004/0220439 A1* | 11/2004 | Williams | C07C 5/2702 585/477 |
| 2008/0237132 A1 | 10/2008 | Hotier | |
| 2010/0249484 A1* | 9/2010 | Stewart | C07C 7/12 585/820 |
| 2011/0226604 A1 | 9/2011 | Bresler | |
| 2012/0116144 A1 | 5/2012 | Schaefer et al. | |
| 2012/0157744 A1* | 6/2012 | Pieper | C10G 25/12 585/822 |
| 2012/0241384 A1 | 9/2012 | Porter | |
| 2013/0153501 A1 | 6/2013 | Frey et al. | |
| 2013/0158332 A1 | 6/2013 | Rauch et al. | |
| 2013/0158335 A1 | 6/2013 | Corradi | |

OTHER PUBLICATIONS

PCT International Search Report for PCT/US2014/053981, mailing date Dec. 10, 2014, Applicant file reference H039336.

* cited by examiner

*Primary Examiner* — Tam M Nguyen

(57) ABSTRACT

Methods and systems for separating para-xylene are disclosed. In one exemplary embodiment, a method for separating para-xylene includes the steps of providing a feed stream including para-xylene and other $C_8$ aromatic hydrocarbons to a first adsorbent bed within a radial flow simulated moving bed chamber and providing a desorbent stream to a second bed within the radial flow simulated moving bed chamber. The method further includes circulating the feed stream and the desorbent stream radially within the radial flow simulated moving bed chamber to third and fourth beds within the radial flow simulated moving bed chamber. Still further, the method includes withdrawing an extract stream including the para-xylene from the third bed and withdrawing a raffinate stream including the other $C_8$ aromatic hydrocarbons from the fourth bed.

11 Claims, 5 Drawing Sheets

METHODS AND SYSTEMS FOR SEPARATING PARA-XYLENE USING A RADIAL FLOW SIMULATED MOVING BED CHAMBER

TECHNICAL FIELD

The present disclosure generally relates to methods and systems for separating aromatic hydrocarbons. More particularly, the present disclosure relates to methods and systems for separating para-xylene using a radial flow simulated moving bed chamber.

BACKGROUND

Continuous separation processes are commonly used for the selective adsorption of para-xylene from a mixture of $C_8$ aromatics. Generally, the processes use a solid adsorbent that preferably retains the para-xylene in order to separate the para-xylene from the rest of the mixture. Often, the solid adsorbent is in the form of a simulated moving bed, where the bed of solid adsorbent is held stationary, and the locations at which the various streams enter and leave the bed are periodically moved. The adsorbent bed itself is usually a succession of fixed sub-beds or modules. The shift in the locations of the liquid input and output in the direction of the fluid flow through the bed simulates movement of the solid adsorbent in the opposite direction.

Moving the locations of the liquid input and output is accomplished by a fluid tracking device known generally as a rotary valve, which works in conjunction with distributors located between the adsorbent sub-beds. The rotary valve accomplishes moving the input and output locations by directing the liquid introduction or withdrawal lines to specific distributors located between the adsorbent sub-beds. After a specified time period, called the step time or hold period, the rotary valve advances one index to the next valve position and redirects the liquid inputs and outputs to the distributors immediately adjacent and downstream of the previously used distributors. Each advancement of the rotary valve to the next valve position is generally called a valve step, and the completion of all the valve steps is called a valve cycle.

The principle liquid inputs and outputs of the adsorbent system include four separate streams, namely the feed, the extract, the raffinate, and the desorbent. Each stream flows into or out of the adsorbent system at a particular flow rate, and each rate is independently controlled. The feed, which is introduced to the adsorbent system, contains the para-xylene that is to be separated from the other components in the feed stream. The desorbent, which is introduced to the adsorbent system, contains a liquid capable of displacing feed components from the adsorbent. The extract, which is withdrawn from the adsorbent system, contains the separated para-xylene, which was selectively adsorbed by the adsorbent, and the desorbent liquid. The raffinate, which is withdrawn from the adsorbent system, contains other $C_8$ aromatic components of the feed that are less selectively adsorbed by the adsorbent, and desorbent liquid.

The four principal streams are spaced strategically throughout the adsorbent system and divide the sub-beds into four zones, each of which performs a different function. Zone I contains the adsorbent sub-beds located between the feed input and the raffinate output, and the selective adsorption of the para-xylene takes place in this zone. Zone II contains the adsorbent sub-beds located between the extract output and the feed input, and the desorption of components other than the para-xylene takes place in this zone. Zone III contains the adsorbent sub-beds located between the desorbent input and the extract output, and the para-xylene is desorbed in this zone. Finally, Zone IV contains the adsorbent sub-beds located between the raffinate output and the desorbent input. The purpose of zone IV is to prevent the contamination of the para-xylene with other components.

When a larger scale separation is required, the volume required for the solid adsorbent and process flow rate are increased to meet the production rate requirement. The combination of the increase of flow rate, larger bed height and compression stress as a result of packing of the solid adsorbent leads to a high pressure drop across the adsorbent bed. Rigid packing of the solid adsorbent or large size adsorbent particles in the bed can reduce the pressure drop, but there is a tradeoff in inferior process performance.

Accordingly, it is desirable to provide improved methods and systems for separating para-xylene. It is further desirable to provide such methods and systems that are scalable depending on production requirements without suffering an increase in pressure drop or a loss in performance. Furthermore, other desirable features and characteristics of the present disclosure will become apparent from the subsequent detailed description and the appended claims, taken in conjunction with the accompanying drawings and this background of the disclosure.

BRIEF SUMMARY

Methods and systems for separating para-xylene using a radial flow simulated moving bed chamber are disclosed. In one exemplary embodiment, a method for separating para-xylene includes the steps of providing a feed stream including para-xylene and other $C_8$ aromatic hydrocarbons to a first adsorbent bed within a radial flow simulated moving bed chamber and providing a desorbent stream to a second bed within the radial flow simulated moving bed chamber. The method further includes circulating the feed stream and the desorbent stream radially within the radial flow simulated moving bed chamber to third and fourth beds within the radial flow simulated moving bed chamber. Still further, the method includes withdrawing an extract stream including the para-xylene from the third bed and withdrawing a raffinate stream including the other $C_8$ aromatic hydrocarbons from the fourth bed.

In another exemplary embodiment, a system for separating para-xylene includes a radial flow simulated moving bed chamber comprising a plurality of adsorbent beds configured in an annular ring. The system further includes at least four channels positioned at a bottom portion of the simulated moving bed chamber fluidly connected with first, second, third, and fourth ones of the plurality of adsorbent beds for providing or withdrawing a respective one of a feed stream comprising para-xylene and other $C_8$ aromatic hydrocarbons, a desorbent stream comprising a desorbent material, an extract stream, and a raffinate stream. Still further, the system includes a rotary valve positioned externally to the simulated moving bed chamber for directing the flow of the respective feed, desorbent, extract, and raffinate streams to a respective one of the four channels.

BRIEF DESCRIPTION OF THE DRAWINGS

The para-xylene separation systems and associated methods will hereinafter be described in conjunction with the following drawing figures, wherein like numerals denote like elements, and wherein.

DETAILED DESCRIPTION

Figure 1:
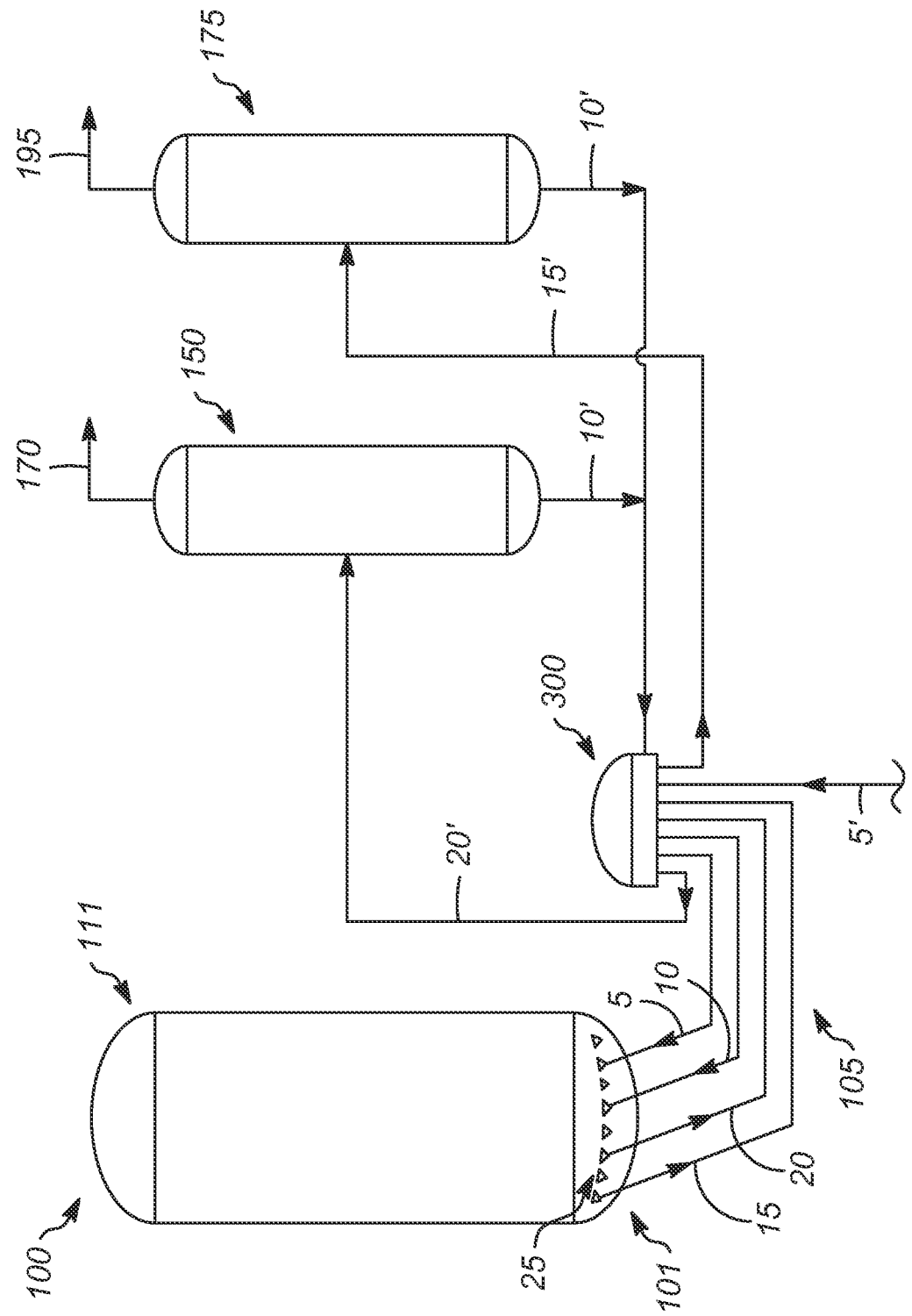
FIG. 1 is a process flow diagram illustrating a method implemented on a para-xylene separation system in accordance with various embodiments of the present disclosure.

The following detailed description is merely exemplary in nature and is not intended to limit the disclosure or the application and uses of the disclosed embodiments. All of the embodiments and implementations of the para-xylene separation systems and associated methods described herein are exemplary embodiments provided to enable persons skilled in the art to make or use the same and not to limit their scope, which is defined by the claims. Furthermore, there is no intention to be bound by any expressed or implied theory presented in the preceding technical field, background, brief summary, or the following detailed description.

Adsorptive separation is applied to the recovery of a variety of hydrocarbons and other chemical products, including aromatic hydrocarbons. Aromatic hydrocarbon separations include mixtures of dialkyl-substituted monocyclic aromatics and of dimethyl naphthalenes. A major commercial application, to which the following description of the embodiments is directed, is the recovery of para-xylene from mixtures of $C_8$ aromatics, due to high purity requirements for these products. As used herein, the term high purity is defined as at least about 99.5 wt.-% of the desired product, and preferably at least about 99.7 wt.-%. Such $C_8$ aromatics usually are derived within an aromatics complex by the catalytic reforming of naphtha followed by extraction and fractionation, or by transalkylation or isomerization of aromatics-rich streams in such complexes. The $C_8$ aromatics generally include a mixture of xylene isomers and ethylbenzene. Processing of $C_8$ aromatics using simulated-moving-bed adsorption generally is directed to the recovery of high-purity para-xylene.

Embodiments of the present disclosure are generally directed to the separation of such aromatics using a radial flow separation scheme. The benefits of a radial flow scheme, as compared to a traditional axial flow scheme, are numerous. For example, as adsorbents improve, less adsorbent is needed for a given unit of feed. To maintain good flow distribution within the system, a minimum bed depth must be maintained. Once this minimum bed depth is reached, the chamber diameter must be increased for increased unit capacity. As the chamber diameter increases costs increase significantly. Further, above a size of about 9 meters, the availability of facilities to fabricate a chamber of such size, along with the transportation of the chamber, become significant issues. If the bed depth is increased to reduce the chamber diameter, system hydraulics increase significantly. This increase in hydraulics will increase operating costs and may cause limits of other system equipment to be exceeded. In a radial bed system, in contrast to a traditional axial flow system, to increase system capacity, the chamber size is increased both in height and diameter with height being the first variable to be increased. Therefore, issues associated with system hydraulics and excessive unit size are significantly reduced. Further, in traditional axial stacked beds, adsorbent bed pressure drops axially. Therefore, the internal support structure of the chamber must withstand a large cumulative pressure drop. In contrast, in a radial bed system, pressure drops do not stack to generate a cumulative load, due to the radial flow path.

FIG. 1 is a process flow diagram illustrating a method implemented on a para-xylene separation system in accordance with various embodiments of the present disclosure. The process sequentially contacts a feed stream 5 with adsorbent contained in the adsorbent chamber and a desorbent stream 10 to separate an extract stream 15 and a raffinate stream 20. The various streams involved in simulated moving bed adsorption as illustrated in FIG. 1 and discussed further below may be characterized as follows. A "feed stream" is a mixture containing one or more extract components or preferentially adsorbed components and one or more raffinate components or non-preferentially adsorbed components to be separated by the process. The "extract stream" includes the extract component, usually the desired product, which is more selectively or preferentially adsorbed by the adsorbent. The "raffinate stream" includes one or more raffinate components which are less selectively adsorbed or non-preferentially adsorbed. "Desorbent" refers to a material capable of desorbing an extract component, which generally is inert to the components of the feed stream and easily separable from both the extract and the raffinate, for example, via distillation.

In the simulated moving bed countercurrent flow system, progressive shifting of multiple liquid feed and product ports 25 positioned on a lower end 101 of a radial flow adsorbent chamber 100 simulate the radial movement of adsorbent contained in the chamber. The chamber 100 contains multiple beds of adsorbent in stationary segments of the chamber 100, as will be described in greater detail below with regard to FIG. 3. The chamber 100 has a number of ports 25 relating to the number of beds of adsorbent, and the position of the feed stream 5, desorbent stream 10, extract stream 15, and raffinate stream 20 are shifted along the ports 25 to simulate a moving adsorbent bed. Circulating liquid comprising desorbent, extract, and raffinate circulates through the chamber 100 through one or more pumps (not specifically shown in FIG. 1). A rotary disc type valve 300 effects the shifting of the streams in the adsorbent chamber 100 to simulate countercurrent flow. Although the rotary disc valve 300 is described herein, other systems and apparatus for shifting the streams along the adsorbent chamber are also contemplated herein, including systems utilizing multiple valves to control the flow of the streams to and from the adsorbent chamber 100.

The person skilled in the art will be aware that a typical axial stacked bed unit, known in the prior art, typically uses two chambers (instead of the single chamber 100 disclosed herein). The purpose of using two chamber in such systems is to reduce the complexity of the internal piping structures, size of the unit, and the cumulative pressure drop load, which can be significant in axial flow chambers as noted above. However, using two chambers increases the facility cost and the structural footprint. In contrast, a radial flow system as disclosed herein can easily incorporate all of the beds into a single chamber 100.

The extract stream 15 and raffinate stream 20 from the illustrated schemes contain desorbent in concentrations relative to the respective product from the process of between 0% and 100%. The desorbent generally is separated from raffinate and extract components by conventional fractionation in, respectively, raffinate column 150, which is fed by stream 20', and extract column 175, which is fed by stream 15', as illustrated in FIG. 1, and recycled to a stream 10' to be returned to the process. FIG. 1 shows the desorbent as a lower end product from the respective column, implying that the desorbent is heavier than the extract or raffinate. Different commercial units for the separation of $C_8$ aromatics employ either light or heavy desorbents, and thus in some applications the desorbent may be separated at a different location along the fractionation columns 150 and 175. The raffinate product 170 and extract product 195 from the process are recovered from the raffinate stream and the extract stream in the respective columns 150 and 175. The extract product 195 from the separation of $C_8$ aromatics usually includes principally one paraxylene, with the raffinate product 170 being principally non-adsorbed $C_8$ aromatics and ethylbenzene. A feed stream 5' provides fresh feed to the rotary valve 300 for distribution to feed line 5.

The liquid streams, e.g., the streams of feed 5, desorbent 10, raffinate 20, and extract 15 entering and leaving the adsorbent chamber 100 via the ports 25 effectively divide the adsorbent chamber 100 into separate zones, which move as the streams are shifted along the ports 25. It should be noted that while much of the discussion herein refers to FIG. 1 and the location of the streams in FIG. 1, FIG. 1 illustrates only a current location of the streams at a single step or a snapshot of the process as the streams typically shift at different steps of a cycle. As the streams shift, the fluid composition and the corresponding zones shift therewith. In one example, the streams each progress a single port 25 for each step and each stream occupies each port 25 one time during an entire cycle. According to one example, the streams are stepped simultaneously to subsequent ports 25 by rotating the rotary valve 300, and are maintained at a particular port 25 or step for a predetermined step-time interval.

Figure 2:
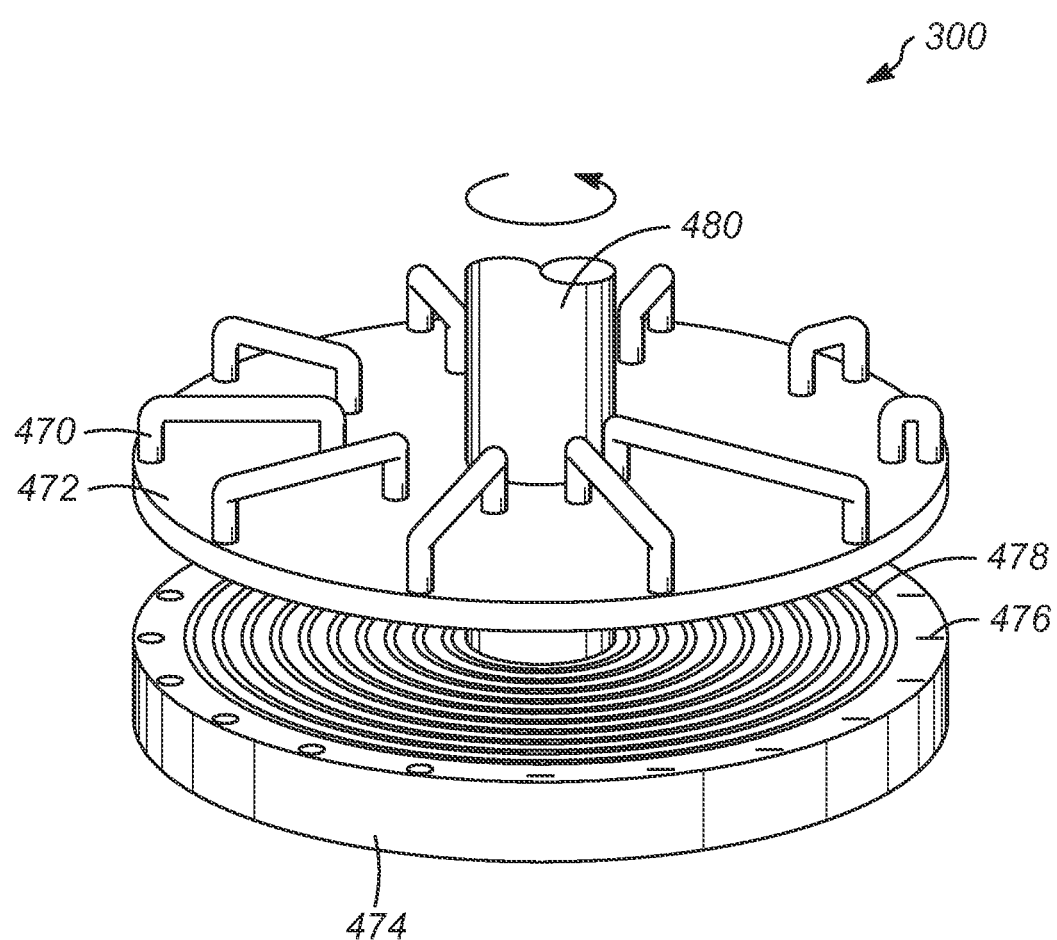
FIG. 2 is a perspective view of a rotary valve suitable for use with the process flow illustrated in FIG. 1.

Adverting momentarily to FIG. 2, a simplified exploded diagram of an exemplary rotary valve 300 for use in an adsorptive separation system and process is depicted. A base plate 474 includes a number of ports 476. The number of ports 476 equal the total number of transfer lines on the chamber(s). The base plate 474 also includes a number of tracks 478. The number of tracks 478 equal the number of net input, output, and flush lines for the adsorptive separation unit (not shown in FIG. 2). The net inputs, outputs, and flush lines are each in fluid communication with a dedicated track 478. Crossover lines 470 place a given track 478 in fluid communication with a given port 476. In one example, the net inputs include a feed input and a desorbent input, the net outputs include an extract output and a raffinate output, and the flush lines include between about one and about four flush lines. As the rotor 480 rotates as indicated each track 478 is placed in fluid communication with the next successive port 476 by crossover line 470. A sealing plate 472 is also provided.

In one embodiment, there are between about 4 and 100 ports 25, between about 12 and 48 ports in another embodiment, and between about 20 and 30 ports in yet another embodiment, and a number of corresponding transfer lines 105, which may or may not be equal to the number of ports 25. In one example, the adsorptive separation chamber 100 includes about 24 ports 25 and each stream is shifted to each of the 24 ports 25 during a complete cycle so that each stream occupies each port 25 and corresponding transfer line 105 during the cycle. In this example, a cycle may be between about 20 and about 40 minutes in one embodiment and between about 22 and 35 minutes in another embodiment. In one embodiment, a step-time interval is between about 30 seconds and about two minutes. In another embodiment, the step-time interval is between about 45 seconds and about one minute thirty seconds. In yet another embodiment, the step-time interval is between about 50 seconds and about one minute and 15 seconds. An example of a step-time interval may be about 1 minute.

Figure 3:
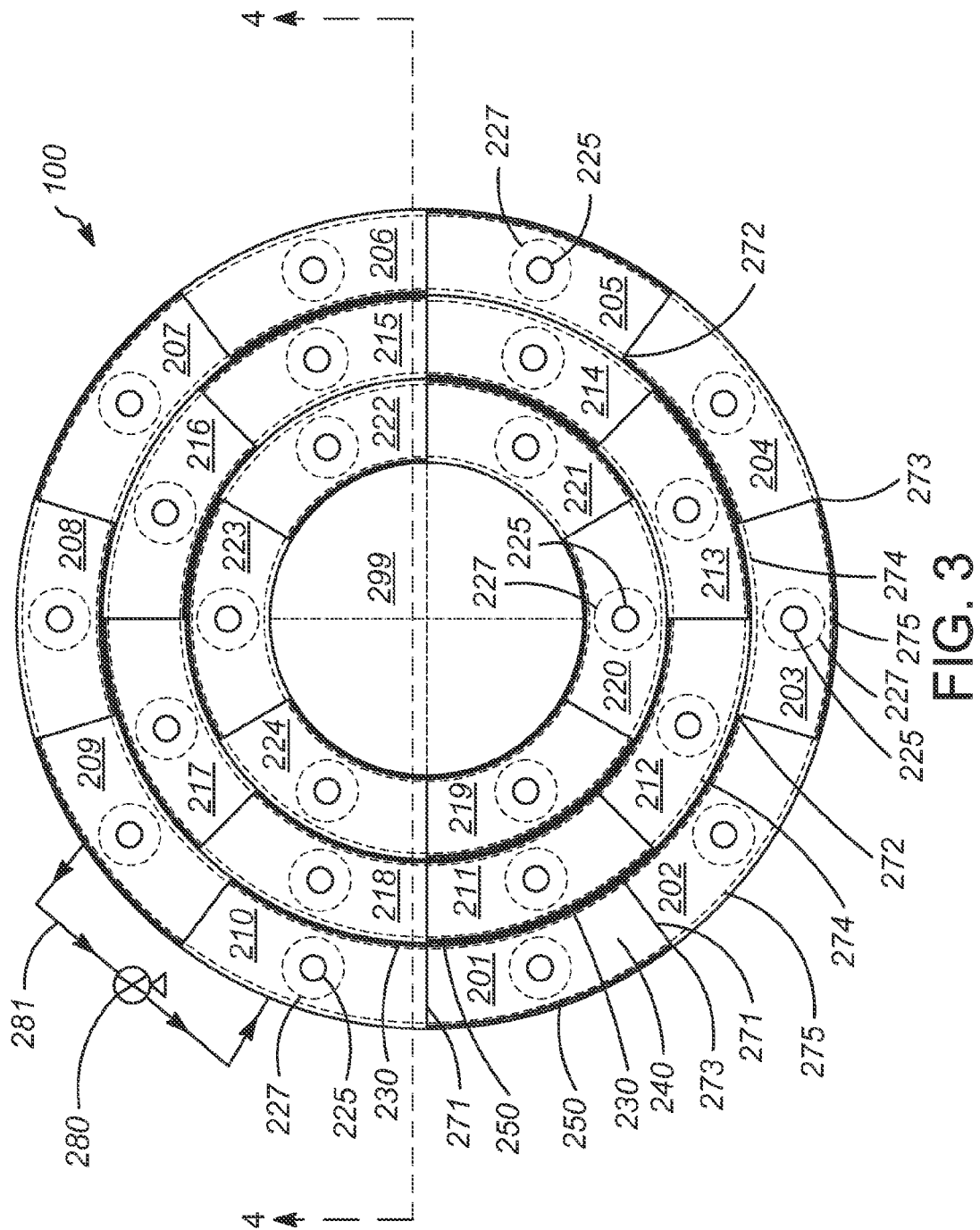
FIG. 3 is a top cross-sectional view through a radial flow para-xylene separation chamber suitable for use with the process flow illustrated in FIG. 1.

Each of the zones described above generally are effected through multiple stationary segments or bed, as will be described in greater detail with regard to FIG. 3. The positions of the various streams 5, 10, 15, and 20 described are structurally separated from one another by a horizontal liquid collection/distribution grid. Each grid is connected to a transfer line 105 defining a transfer point at which process streams enter and leave the adsorbent chamber 100. This arrangement facilitates the distribution of fluids within the chamber 100 by eliminating channeling and other inefficiencies, prevents convective back-mixing of fluid in a direction opposite to that of primary fluid flow, and prevents migration of adsorbent through the chamber. Each of the zones described above may include a plurality of 2 to 10, and more usually 3 to 8, beds. An exemplary simulated moving bed adsorption unit includes 24 beds of adsorbent.

With reference back to FIG. 1, when a transfer line 105 at an access point 25 that is being used to transport a particular stream into or out of the adsorbent chamber is left idle at the end of a step it will remain full of the compounds forming that stream until these compounds are removed from the line 105 by a second flowing stream. In this regard, it should be noted that only active transfer lines 105, i.e. those lines presently facilitating flow of fluid therethrough, are illustrated in FIG. 1, although intermediate transfer lines are present at each of the ports 25 along the chamber 100 to facilitate fluid flow upon shifting of the fluid streams to subsequent ports 25. The residual fluid or compounds left in the now unused transfer line 105, after a stream shifts to a subsequent transfer line 105, will therefore be either withdrawn from the process as the initial part of a process stream removed from the process or forced into the adsorbent chamber when the transfer line 105 carries a stream into the adsorbent chamber.

In contrast to the configuration illustrated in FIG. 1, a typical axial stacked bed unit with two chambers requires a significant amount of piping between the two chambers and the rotary valve. A radial flow system with a common area (chamber bottom region 101) for all ports 25 significantly reduces the piping volume and length. This reduction in piping will improve performance by reduction in flush volumes and piping hydraulic losses.

Figure 4:
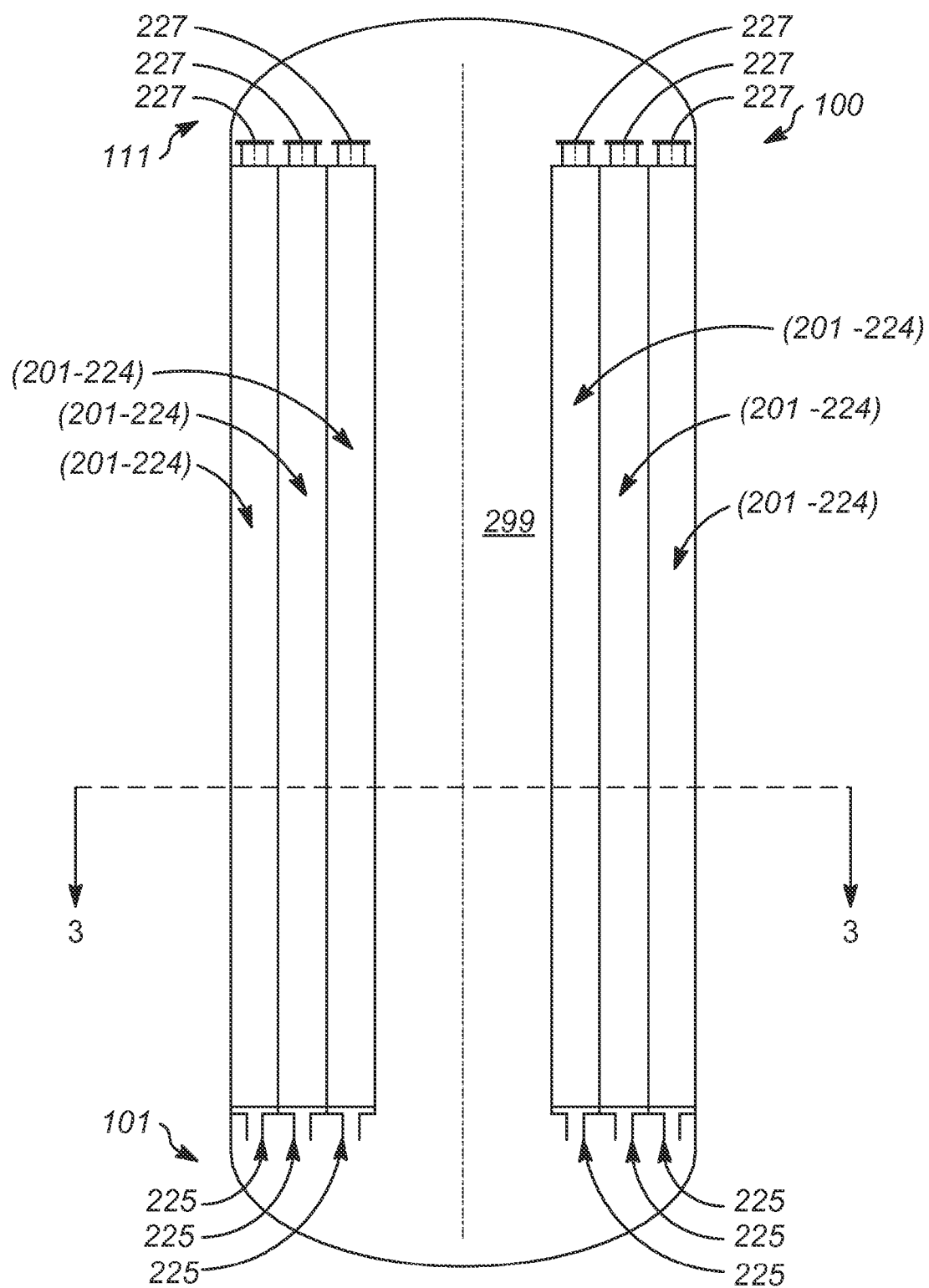
FIG. 4 is a side cross-sectional view through the radial flow para-xylene separation chamber shown in FIG. 3.

As initially noted above, the simulated moving bed chamber 100 operates with fluid flowing in the radial direction in each of the beds. A top cross-section diagram of an exemplary radial flow chamber 100 is given in FIG. 3, and a side cross-sectional view thereof is given in FIG. 4. The chamber 100 includes a plurality of inlet/outlet channels 225 that correspond to and are fluidly connected with each of the ports 25 shown in FIG. 1. The inlet/outlet channels, in turn, are fluidly connected with a respective one of the beds 201-224 (i.e., 24 beds are included in the embodiment illustrate in FIGS. 3 and 4. The inlet/outlet channels 225 are individually employed to receive/transfer fluid from/to the beds 201-224, and to/from the ports 25. In contrast, a typical axial stacked bed unit includes a significant amount of internal piping, and this internal piping creates non-uniform flow paths and shadowing. The internal piping also limits the minimum bed depth based on physical limitations. As shown herein, the exemplary radial flow chamber 100 has no internal piping within the adsorbent bed.

With regard to the solid adsorbent disposed within the chamber 100, the person skilled in the art will appreciate that a typical axial stacked bed must load the adsorbent as the internal piping structures are being installed, which significantly increases the time required to load a chamber. This loading time is often the limiting step, and can cost a user of such system significantly in term of lost production. In contrast, a radial flow system as disclosed herein can easily be unloaded and reloaded using the adsorbent loading manways 227 positioned in an upper region 111 of the chamber 100 (alternatively, unloading nozzles may be employed in some embodiments). With the radial flow scheme, as noted previously, all of the inlet/outlet channels 225 are positioned at the bottom region 101 of the chamber 100. This configuration leaves the upper region 111 available for use as an adsorbent loading/unloading region.

Each bed of the plurality of beds 201-224 includes an inner fluid transfer segment 230, a stationary phase segment 240, and an outer fluid transfer segment 250. For simplicity of illustration, the segments 230, 240, and 250 will only be referenced by numerals at bed 201, although it should be appreciated that each of beds 201-224 could be similarly referenced. The stationary phase segments 240 communicate with the inlet/outlet channels 225 for providing/withdrawing fluid from each of the beds 201-224. Each of the inner fluid transfer segments 230 is isolated from each other by a partition plate 271. Every other partition plate 271 that separates the inner fluid transfer segments 230 has a circulation mechanism 272 that allows the two adjacent inner fluid transfer segments 230 to communicate to each other. The circulation mechanism 272 may be embodied as a plurality of openings or channels in the first partition plate 271, piping or tubing connecting the two adjacent beds, the removal of the partition plate 271 between the two adjacent beds, or any other similar structure. Each inner fluid transfer segment 230 can only communicate with one of the two adjacent inner fluid transfer segments 230 directly though the circulation mechanism 272.

The stationary phase segments 240 are radially outside of the inner fluid transfer segments 230. Each of the stationary phase segments 240 is isolated from adjacent stationary phase segments by the partition plate 271 and communicates with the corresponding inner fluid transfer segment 230. The outer fluid transfer segments 250 are radially outside of the stationary phase segments 240. Each outer fluid transfer segment 250 communicates with the corresponding stationary phase segment 240 and is separated from adjacent outer fluid transfer segments by the partition plates 271. Every other outer fluid transfer segment 250 communicates directly with the adjacent outer fluid transfer segment group by a circulation mechanism 273. The circulation mechanism 273 may be embodied as a plurality of openings or channels in the first partition plate 271, piping or tubing connecting the two adjacent beds, the removal of the partition plate 271 between the two adjacent beds, or any other similar structure.

In one exemplary implementation, fluid entering into the stationary phase segment 240 of bed 201 flows through the stationary phase segment 240 wherein it contacts with the solid adsorbent. It thereafter circulates radially to bed 202 via an outer transfer segment 273. The fluid then flows into the stationary phase segment 240 of bed 202 wherein it contacts with the solid adsorbent. It thereafter circulates radially to bed 203 via inner fluid transfer segment 230. The fluid continues in this manner through each of the beds 201-224, in sequential order. As shown in FIG. 3, the beds 201-224 are configured annularly in three concentric rings. Of course a configuration with one, two, or more than three rings would also be possible, with more or fewer beds in a given embodiment. Fluid flow radially inward from an outer concentric ring to the next inner concentric ring is accomplished by fluid flow from an inner fluid transfer segment 230 to an outer fluid transfer segment 250 (for example, from the inner fluid transfer segment 230 of bed 210 to the outer fluid transfer segment 250, as shown in FIG. 3). Radially inward from the innermost ring of a given embodiment may be a cylindrical void space 299 where no fluid flow occurs.

Fluid transfer between the respective segments 230, 240, and 250 may be accomplished, in one embodiment, by a plurality of inner porous elements 274 and a plurality of outer porous elements 275. Each of the inner porous elements 274 is positioned between the inner fluid transfer segment 230 and the corresponding stationary phase segment 240. Each of the outer porous elements 275 is positioned between the stationary phase segment 240 and the corresponding outer fluid transfer segment 250. To properly distribute the fluid into the stationary phase segment 240, the opening on the porous elements 274, 275 are preferably angularly distributed evenly. The inner porous elements 274 and the outer porous elements 275 may be embodied as a screen, a perforated plate, or a similar structure. Additionally, in order to ensure adequate mixing between flows entering the beds from below and flows transferring radially from one bed to another, there may be provided one or more fluid mixing apparatus. Fluid mixing apparatus may include a distributor, flow restrictor, tubing or piping, etc., as may be necessary for a particular design. It is expected that a person having ordinary skill in the art will be capable of performing computational fluid dynamics (CFD) analysis on any given implementation or design to determine any possible poor mixing areas or "dead spots," in any of the segments 230, 240, and 250 of any of the beds 201-224, and implement a known fluid mixing apparatus in an appropriate location to improve the flow in such areas.

Every bed 201-224, in the stationary phase segments 240, is loaded with a solid adsorbent, and the solid adsorbent is confined by the inner and outer porous elements 274, 275 and the partition plates 271. The inner fluid transfer segments 230 are segmented and bounded by the partition plates 271 and the inner porous element 274. The outer fluid transfer segments 250 are bounded by the partition plate 271 and outer porous element 275. The numbers of the inner fluid transfer segments 230, the outer fluid transfer segments 250, and the stationary phase segments 240 are the same.

To keep the fluid moving from bed to bed in a radial flow, one or more fluid moving devices 280, such as a pump, may be provided to circulate the fluid. The device 280 may be connected to inlet/outlet 225 channels 225 located at the bottom area 101 of two adjacent fluid distribution segments 230 (such as those for beds 209 and 210 as shown in FIG. 3), via a fluid line 281. The process fluid is circulating in a counterclockwise direction as shown in FIG. 3. To simulate the movement of the stationary phase solid adsorbent, the rotary device 300 rotates in in the fluid flow direction to simulate the counter current movement of the stationary phase to the pump 280 around the fluid flow.

Figure 5:
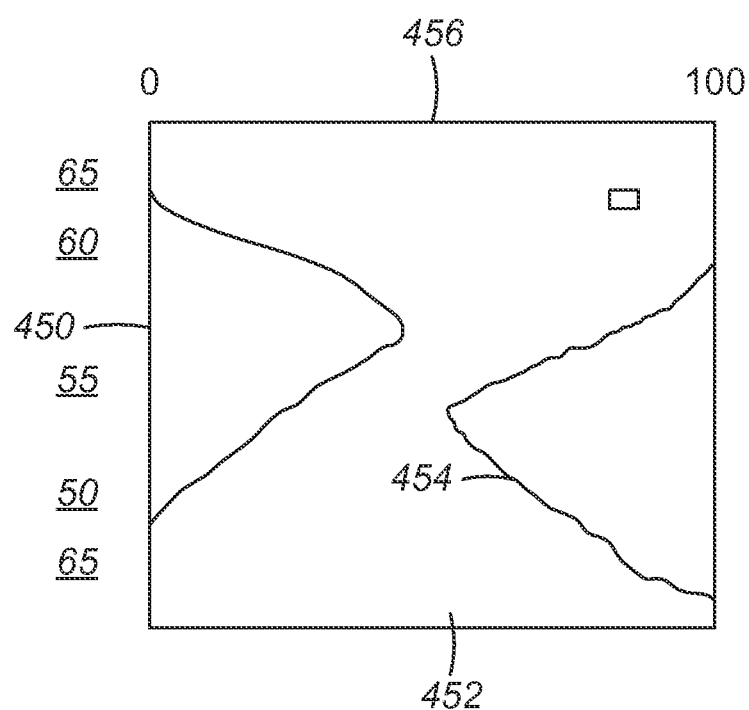
FIG. 5 is a compositional diagram of fluid within the radial flow para-xylene separation chamber shown in FIGS. 3 and 4.

FIG. 5 provides a snapshot of the compositional profile of the fluid within a radial flow adsorptive separation chamber 100 and the corresponding zones into which the adsorptive separation chamber 100 is divided. The adsorption zone 50 is located between the feed inlet stream 5 and the raffinate outlet stream 20. In this zone, the feed stream 5 contacts the adsorbent, an extract component is adsorbed, and a raffinate stream 20 is withdrawn. As illustrated in FIG. 5, the raffinate stream 20 may be withdrawn at a location where the composition includes raffinate fluid 454 and little if any extract fluid 450. Immediately upstream with respect to fluid flow is the purification zone 55, defined as the adsorbent between the extract outlet stream 15 and the feed inlet stream 5. In the purification zone 55, the raffinate component is displaced from the non-selective void volume of the adsorbent and desorbed from the pore volume or surface of adsorbent shifting into this zone by passing a portion of extract stream material leaving the desorption zone 60. The desorption zone 60, upstream of the purification zone 55, is defined as the adsorbent between the desorbent stream 10 and the extract stream 15. The desorbent passing into this zone displaces the extract component which was adsorbed by previous contact with feed in the adsorption zone 50. The extract stream 15 may be withdrawn at a location of the chamber 100 that includes extract fluid 450 and little if any raffinate fluid 454. A buffer zone 65 between the raffinate outlet stream 20 and the desorbent inlet stream 10 prevents contamination of the extract, in that a portion of the desorbent stream enters the buffer zone to displace raffinate material present in that zone back into the adsorption zone 50. The buffer zone 65 contains enough adsorbent to prevent raffinate components from passing into the desorption zone 60 and contaminating the extract stream 15.

As such, the present disclosure provides various exemplary embodiments of methods and systems for separating para-xylene using a radial flow simulated moving bed chamber. The methods and systems are beneficially scalable depending on production requirements without suffering an increase in pressure drop and a corresponding loss in performance.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes may be made in the processes without departing from the scope defined by the claims, which includes known equivalents and foreseeable equivalents at the time of this disclosure.

What is claimed is:

1. A method for separating para-xylene comprising the steps of:
   providing a feed stream comprising para-xylene and other C8 aromatic hydrocarbons to a first adsorbent bed within a radial flow simulated moving bed chamber;
   providing a desorbent stream comprising a desorbent material to a second bed within the radial flow simulated moving bed chamber;
   circulating the feed stream and the desorbent stream radially within the radial flow simulated moving bed chamber to third and fourth beds within the radial flow simulated moving bed chamber;
   withdrawing an extract stream comprising the para-xylene and desorbent material from the third bed; and
   withdrawing a raffinate stream comprising the other C8 aromatic hydrocarbons and desorbent material from the fourth bed.

2. The method of claim 1, wherein providing a feed stream comprises providing a catalytically reformed naphtha stream.

3. The method of claim 1, wherein providing the feed stream comprises providing the feed stream to a radial flow simulated moving bed chamber comprising 24 adsorbent beds.

4. The method of claim 3, wherein providing the feed stream comprises providing the feed stream to a radial flow simulated moving bed chamber comprising three annular rings of adsorbent beds.

5. The method of claim 1, wherein providing the feed stream comprises providing the feed stream to a bottom region of the simulated moving bed chamber.

6. The method of claim 5, wherein providing the desorbent stream comprises providing the feed stream to a bottom region of the simulated moving bed chamber.

7. The method of claim 6, wherein withdrawing the extract stream comprises withdrawing the extract stream from a bottom region of the simulated moving bed chamber.

8. The method of claim 7, wherein withdrawing the raffinate stream comprises withdrawing the raffinate stream from a bottom region of the simulated moving bed chamber.

9. The method of claim 1, further comprising distilling the extract stream to separate the para-xylene from the desorbent material.

10. The method of claim 9, further comprising distilling the raffinate stream to separate the other C8 aromatic hydrocarbons from the desorbent material.

11. A method for separating para-xylene comprising the steps of:
    providing a feed stream comprising para-xylene and other C8 aromatic hydrocarbons to a first adsorbent bed within a radial flow simulated moving bed chamber, wherein providing a feed stream comprises providing a catalytically reformed naphtha stream;
    providing a desorbent stream comprising a desorbent material to a second bed within the radial flow simulated moving bed chamber;
    circulating the feed stream and the desorbent stream radially within the radial flow simulated moving bed chamber to third and fourth beds within the radial flow simulated moving bed chamber;
    withdrawing an extract stream comprising the para-xylene and desorbent material from the third bed;
    withdrawing a raffinate stream comprising the other C8 aromatic hydrocarbons and desorbent material from the fourth bed; and
    further comprising distilling the extract stream to separate the para-xylene from the desorbent material.

* * * * *